(12) United States Patent
Adams et al.

(10) Patent No.: US 7,981,673 B2
(45) Date of Patent: Jul. 19, 2011

(54) PROCESS FOR THE MATURATION OF DENDRITIC CELLS AND A VACCINE

(75) Inventors: Malcolm Adams, Cardiff (GB); Cyril Donninger, Sandton (ZA)

(73) Assignee: Biociones (Propietary) Limited, Sandton (ZA)

( * ) Notice: Subject to any disclaimer, the term of this patent is extended or adjusted under 35 U.S.C. 154(b) by 0 days.

(21) Appl. No.: 10/486,288

(22) PCT Filed: Aug. 8, 2002

(86) PCT No.: PCT/IB02/03116
§ 371 (c)(1),
(2), (4) Date: Jul. 29, 2004

(87) PCT Pub. No.: WO03/014335
PCT Pub. Date: Feb. 20, 2003

(65) Prior Publication Data
US 2004/0253722 A1 Dec. 16, 2004

(30) Foreign Application Priority Data
Aug. 8, 2001 (GB) .................................. 0119346.5

(51) Int. Cl.
*C12N 5/08* (2006.01)
(52) U.S. Cl. ....................................................... 435/372
(58) Field of Classification Search ........................ None
See application file for complete search history.

(56) References Cited

U.S. PATENT DOCUMENTS

| | | | | | |
|---|---|---|---|---|---|
| 4,130,641 | A | * | 12/1978 | Ts'o et al. | 514/449 |
| 6,080,726 | A | * | 6/2000 | Ts'o et al. | 514/44 |
| 2002/0071825 | A1 | * | 6/2002 | Schall et al. | 424/85.1 |

FOREIGN PATENT DOCUMENTS

WO     WO 9722349 A1 * 6/1997

OTHER PUBLICATIONS

Cella et al. Maturation, activation, and protection of dendritic cells induced by double-stranded RNA. J Exp Med. vol. 189, No. 5, pp. 821-859, Mar. 1999.*

Lehy et al. Differential activation of influenza A virus endonuclease activity is dependent on multiple sequence differences between the virion RNA and cRNA promoters. J Virol. vol. 76, No. 4, pp. 2019-2023, Feb. 2002.*

(Continued)

*Primary Examiner* — Scott Long
(74) *Attorney, Agent, or Firm* — Buchanan Ingersoll & Rooney PC

(57) ABSTRACT

The invention proves a method of producing mature dendritic cells in vitro, which comprises the step of culturing the immature dendritic cells in the presence of a specifically configured high molecular weight double stranded RNA (dsRNA) polymer. The specifically configured high molecular weight dsRNA polymer is typically selected from the group comprising poly[I]:poly [$C_xU$]; poly [I]:poly [$G_xU$]; poly [A]:poly [$U_xC$]; poly [A]:poly [$U_xG$]; poly [U]:poly [$A_xC$]; poly [U]:poly [$I_xU$]; poly [C]:poly [$G_xA$]; poly [C]:poly [$G_xU$]; poly [G]:poly [$C_xA$]; poly [G]:poly [$C_xU$] and AMPLIGEN® (poly[I]:poly[$C_{12}U$]), where x is on average a number from 3 to 40. The immature dendritic cells may be exposed to an antigen before they are matured, and a vaccine including the antigen-presenting mature dendritic cells can then be prepared. A method of treating cancer, a virus, parasite and microorganism is also disclosed.

15 Claims, 6 Drawing Sheets

Figure 1:
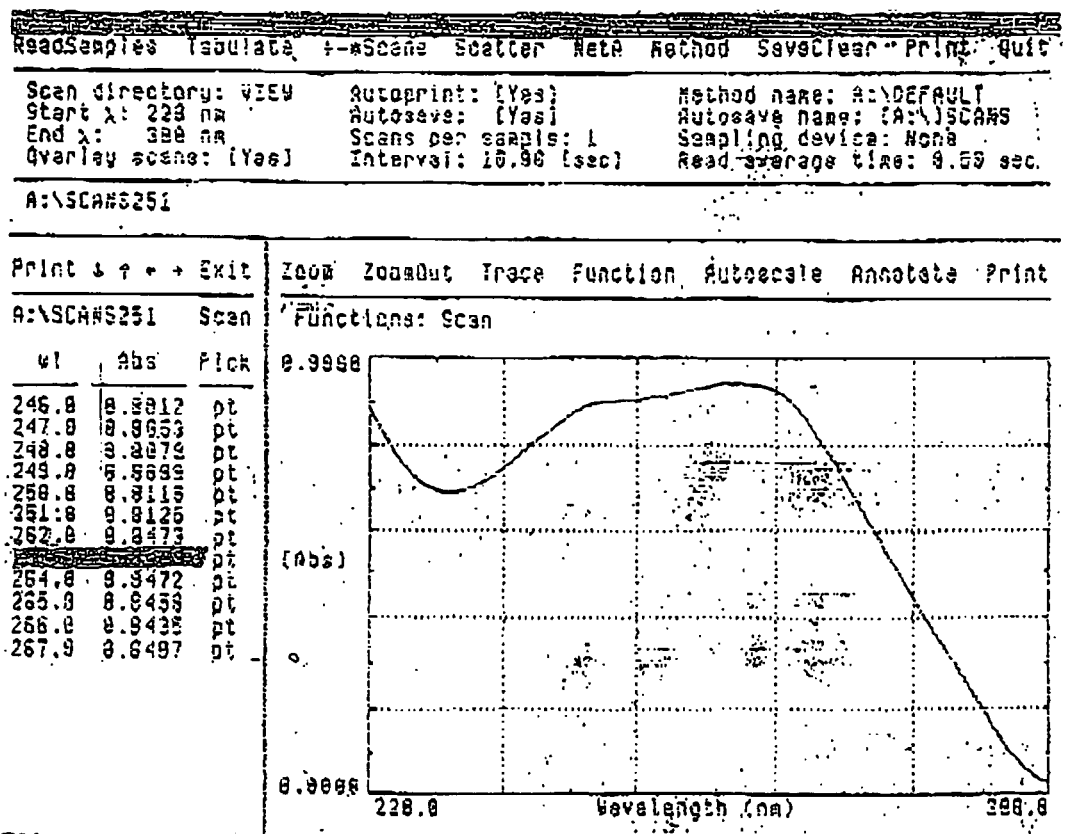

Dendritic cell (DC) culture supernatant IL 12 [P70]

The influence of maturation agents poly [I]: poly [C] and Ampligen® on dendritic cells and time course of IL 12 p70 production by dendritic cells

OTHER PUBLICATIONS

Verdijk et al. Polyriboinosinic polyribocytidylic acid (poly(I:C)) induces stable maturation of functionally active human dendritic cells. J Immunol. vol. 163, No. 1, pp. 57-61, Jul. 1999.*

Kavonian et al. Ultrafiltration: Trends in Sample Prep. pp. 1/4 to 4/4, Feb. 2006.*

Product information sheet for Microcon YM-100 Centrifugal Unit, Catalogue No. 42424, www.millipore.com, printed on Jun. 4, 2006.*

Rotor Speed selection chart.*

Cella et al. (J. Exp. Med. 1999; 189(5): 821-829).*

Rook et al. (Emerging Drugs. 1998; 3:345-352).*

De Clercq (J.Gen Virol. 1977; 37: 619-623).*

Avril et al. (J Immunother 2009; 32: 353-362).*

Navabi et al. (Vaccine. 2009; 27: 107-115).*

Carter, W.A. et al.: Mismatched Double-Stranded RNA, Ampligen (Poly(I); Poly(C12U)), Demonstrates Antiviral and Immunostimulatory Activities in HIV Diseas, International Journal of Immunopharmacology, Elmsford NY, vol. 13, Suppl 1, 1991 pp. 69-76.

Dhodapkar Madav V. et al.: "Rapid Genereation of Broad T-Cell Immunity in Humans After a Single Injection of Mature Dendritic Cells", Journal of Clinical Investigation; vol. 104, No. 2 Jul. 2, 1999 pp. 173-180.

Zitvogel L. et al.: "Therapy of Murine Tumors with Tumor Peptide-Pulsed Dendritic Cells: Dependence on T-Cells, B7 Costimulation, and T Helper Cell 1-Associated Cytokines", Journal of Experiemental Medicine, Tokyo, JP; vol. 183, Jan. 1996 pp. 87-97.

H.Navabi et al., "Ampligen® (poly[I]: poly[$C_{12}U$]: a GMP-grade agent which is a powerful inducer of dendritic cell maturation", Proceedings of Immunology, $12^{th}$ International Immunology Meeting, Montreal, Canada, (2004—pp. 1-9).

Scott M. Hammond et al., "Post-Transcriptional Gene Silencing by Double-Stranded RNA", Nature Reviews (Feb. 2001—vol. 2, pp. 110-119), Macmillan Magazines Ltd.

Phillip A. Sharp, "RNA Interference—2001", Genes & Development (2001—pp. 485-490), Cold Spring Harbor Laboratory Press ISSN 0890-9369/01.

Marc Bauer et al., "Bacterial CpG-DNA Triggers Activation and Maturation of Human CD11c, CD123+Dendritic Cells", (2001—pp. 5000-5007), The American Association of Immunologists 0022-1767/01.

Ichiro Nakamura et al., "Editor-Communicated Paper: Phenotypic Stability of Mature Dendritic Cells Tuned by TLR or CD40 to Control the Efficiency of Cytotoxic T Cell Priming", Microbiol. Immunol. (2004 pp. 211-219).

* cited by examiner

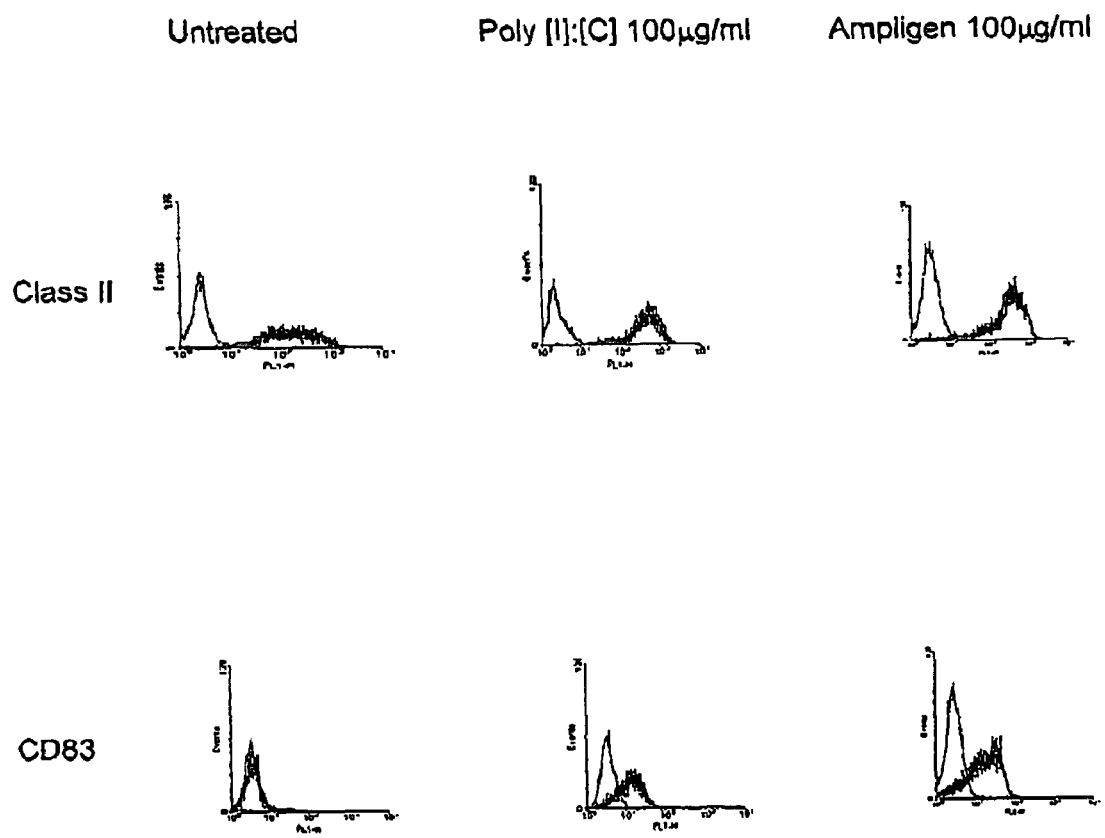
Figure 4. Effect of Poly [I]: poly [C] and Ampligen ® on immature monocyte-derived dendritic cells as determined by class II and CD83.

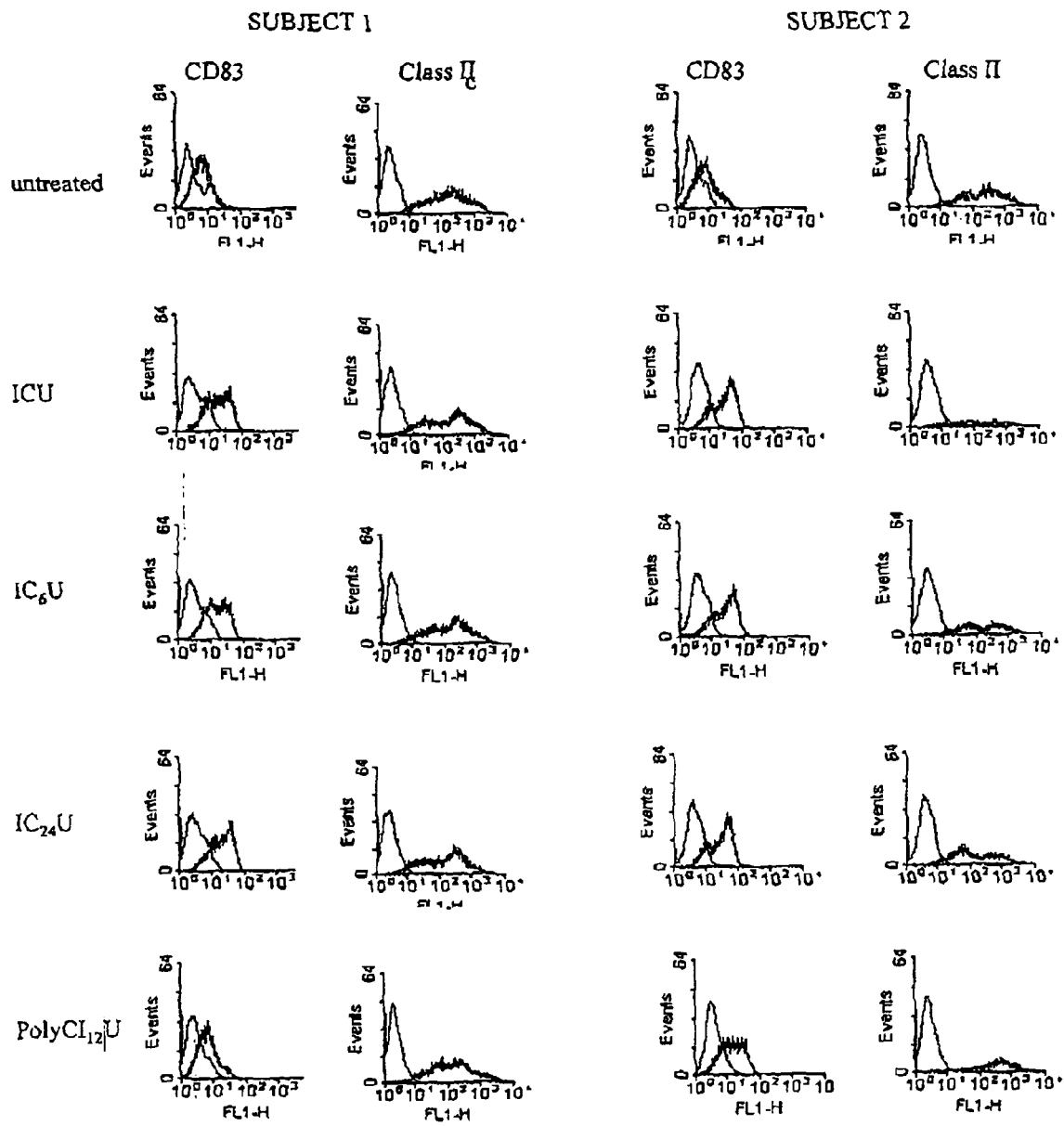
Figure 5. The effects on CD83 and class II expression of dendritic cells from two healthy individuals treated with Poly [I]: Poly [$C_6$U], Poly [I]: Poly [$C_{24}$U] and Poly [C]: Poly [$I_{12}$U]

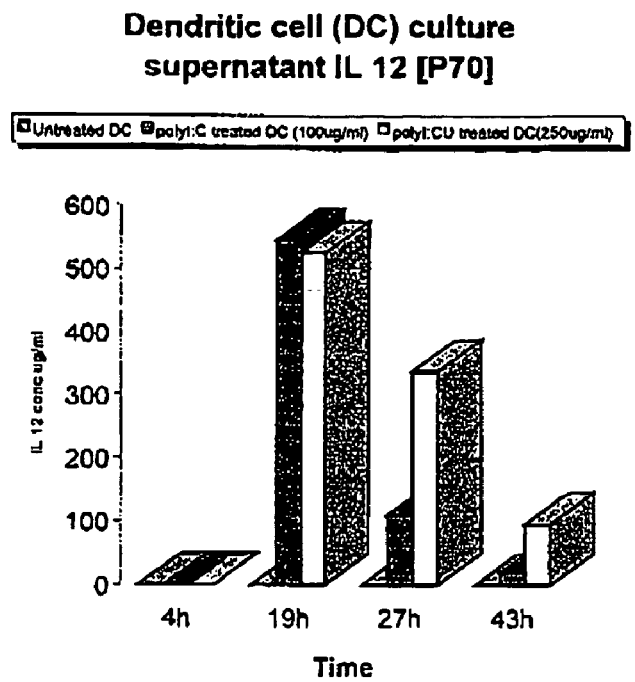
Figure 6. The influence of maturation agents poly [I]: poly [C] and Ampligen® on dendritic cells and time course of IL 12 p70 production by dendritic cells

PROCESS FOR THE MATURATION OF DENDRITIC CELLS AND A VACCINE

BACKGROUND OF THE INVENTION

This invention relates to a method for maturing human dendritic cells, to a method for enhancing production of interleukin 12 (IL 12) from mature dendritic cells, and to a vaccine containing matured dendritic cells producing enhanced levels of IL 12.

It has, been established that cytotoxic CD8+ T-cell lymphocytes (CTL) can recognize and kill tumour cells which present tumour antigens on the cell surface in conjunction with MHC (major histocompatability complex) class I molecules[1]. However, in the majority of patients who are diagnosed with cancer, the patient's cellular immune response is not sufficiently activated in response to tumour antigens, and therefore the patient's body is unable to adequately kill the tumour cells and so defend itself from the further spread of the cancer. Patients may therefore be treated with chemotherapy or radiation therapy, both of which may indiscriminately kill the normal cells and may cause significant toxic side effects to the patient. If the cellular immune response could be sufficiently activated by tumour antigens, then it is possible that the patient's body would be able to eradicate the tumour cells itself, without the undesirable side effects associated with conventional types of cancer treatment.

Therefore, a need exists to therapeutically activate a cancer patient's cellular immune system so that it responds to tumour-associated antigens.

Dendritic cells are among the most powerful antigen-presenting cells for priming both CD8+ cytotoxic T-cells (CTL) and CD4+ T-helper (Th1) responses[2]. They are capable of capturing and processing antigens and migrating to the regional lymph nodes to induce CD8+ T-cell responses[2]. They have the capacity to cross-present exogenous antigens in the context of MHC class I molecules present on the cell surface[3]. These features taken together enable the dendritic cells to present antigen in a manner which is capable of priming both CD8+ and CD4+ T-ell responses, providing a rationale for the use of dendritic cells as a cellular vaccine. However, for this it is necessary to have dendritic cells available in sufficient numbers and in a functionally optimum antigen loaded state.

Murine studies have supported the immunizing capacities of bone marrow-derived dendritic cells propagated in vitro with GM-CSF and interleukin 4 (IL 4), and pulsed with the relevant CTL defined tumour associated epitopes.[4,5] The studies have demonstrated that dendritic cells primed with defined tumour associated antigen peptides are capable of eradicating established tumours expressing the appropriate tumour antigens. These dendritic cell-mediated anti-tumour responses in animal models have been shown to be dependent on CD4+ T-helper (MHC class II) as well as CD8+ (MHC class I) responses and also on the production of Th1 lymphokines[5].

These animal studies have led to a number of phase 1 human clinical trials using mature and immature autologous dendritic cells loaded with tumour antigens. For example, Nestle et al[6] have treated 16 patients with metastatic melanoma with immature GM-CSF/IL 4 monocyte-derived dendritic cells grown in fetal calf serum. Clinical response was seen in 5 out of 16 patients usually durable (2 complete responses and 3 partial responses) with skin, soft tissue, lung and pancreatic metastases. Monocyte-derived dendritic cells pulsed with MAGE-3 tumour specific peptides and matured with TNF-α similarly induced responses in 6 out of 11 patients with skin, lymph node, lung and liver metastases[7]. A significant expansion of MAGE-3 HLA A1-specific CD8+ T-cells was observed in 6 out of 11 patients and response of skin metastases was associated with a CD8+ T-cell infiltrate.

Evidence supporting the efficacy of dendritic cells as immunotherapeutic agents has also been gathered from clinical trials involving patients with metastatic cancers from other types of primary tumours. Immunisation with dendritic cells prepared from the fusion of allogeneic monocytes and autologous tumour cells, and matured with TNF-α, were successful in inducing cellular immune responses in 7 out of 11 patients with metastatic renal cell carcinoma, including 4 complete remissions[8]. GM-CSF/IL 4 immature dendritic cells pulsed with prostate membrane antigen P1 and P2 have been employed in 37 patients with advanced prostate cancer. One complete response and 10 partial responses (>50% reduction in PSA levels or significant resolution on a bone scan) were observed[9]. In a series of 9 patients[10] with advanced cervical cancer who were treated with immature GM-CSF/IL 4 dendritic cells pulsed with allogeneic HPV 16+ve tumour lysate specific HPV specific CTL, response was demonstrated in peripheral blood in 2 out of 2 evaluable (HPV16+HLA 002*) patients after vaccination. In one patient the frequency of HPV16E7 (11-20) rose to 2.2% as detected by class1 tetramers and in the other patient the IFN-γ ELISPOT assay revealed a specific response to 4 HPV 16 E6 and 7 derived CTL epitopes, 1 week and 2 months, respectively, after vaccination. In 1 out of 4 evaluable HPV 16+ patients a specific T-helper response was also observed. T cell immunity as detected by ELISPOT correlated with the DTH response to tumour lysate and these patients followed a favourable clinical outcome (NED of disease 18 months or more after resection of lung metastasis, stable disease for 3 months or more after progression).

Therefore it is feasible to induce clinically relevant specific class I and T-helper responses in patients with metastases from a variety of cancer types using monocyte-derived dendritic cells pulsed with a variety of tumour associated antigens. However, currently no consensus exists with respect to the definition of the immunologically active phenotype, dose, route and loading method for optimum cancer immunization with dendritic cells[11].

It seems mature dendritic cells are likely to be more effective at presenting antigens and triggering CTL and T-helper response than immature dendritic cells[2]. Whilst clinical anti-cancer responses have been observed following immunization with immature dendritic cells it is likely that in these patients dendritic cells may have been at some point matured in vivo by an as yet undefined stimulus. Dendritic cells normally acquire antigens from peripheral tissues in their immature state. Maturation Is characterized by downregulation of their antigen-acquisition capacity, increased expression of MHC and co-stimulatory molecules on their surface, raised level of IL 12 production by them, and altered expression of chemokine receptors[12].

Thus a means for deliberate maturation of dendritic cells in vitro prior to their use for vaccination may offer the advantage of a phenotype with an optimum migratory capacity to lymph nodes to prime T-cells in lymph nodes, an optimum Th1 lymphokine[13] production capacity as well as a stable functional state which is least susceptible to the cancer associated tolerogenic influences such as Interleukin 10[14].

Critical to whether the T-cells are activated or energised by interaction with dendritic cells, appears to be the nature of the "activation" or "danger signal", which may be pathogen-induced or triggered by factors released by stressed, damaged or necrotic cells as originally proposed by Matzinger[15].

However the nature of the optimum "activation" or "danger signal" still remains to be defined, though in vitro data appear to suggest that whatever its ultimate nature it requires to be able to induce maturation of dendritic cells and IL 12 production by the dendritic cells, two properties which are important for optimum CD8+ T-cell response.

Bacterial DNA, CD40 ligand, pro-inflammatory agents such as LPS, viral infections, CpG-oligodeoxynucleotides and heatshock proteins can all initiate maturation of dendritic cells[16-19]. Lymphokines such as TNF-α and type 1 interferons are also known to induce reversible maturation of the dendritic cells[20-21]. In contrast, the supernatant of activated monocytes (monocyte-derived medium) appears to be an agent capable of inducing a stable maturation state, but it is difficult to standardize its quality for clinical use[22]. For clinical immunotherapeutic application of dendritic cells, a stable dendritic cell phenotype which produces high levels of biologically active IL 12, appears to be ideal Poly [I]: poly [C] (polyriboinosinlc:polyribocytidylic acid), a synthetic dsRNA (double stranded RNA), has been found to induce a stable mature phenotype with high expression levels of CD86 and the maturation marker CD83. The mature phenotype is retained for 48 hours after cytokine withdrawal and these mature dendritic cells produce high levels of IL 12 and low levels of IL 10[23]. Activation of dendritic cells with a microbial stimulus (e.g. CpG oligonucleotides) and a range of bacterial stimuli in the absence of a T-cell derived signal appears to be sufficient to release significant levels of IL 12[24]. Under these conditions dendritic cells upregulate CD40 expression and subsequent cross-linking of CD40 can result in further enhanced IL 12 production[24]. The notion that optimal production of IL 12 p70 by dendritic cells involves synergy between CD40 cross-linking and microbial stimulation is compatible with human in vitro studies that demonstrate that the interaction between T-cells and antigen-presenting cells is not sufficient to induce high levels of IL 12 production unless microbial stimuli and/or cytokines are used as the adjuvants, or alternatively IL 12 production is induced by the interaction of the dendritic cells with the T-cells[25-26]. These data emphasize the importance of bacterial stimuli in the production of high levels of IL 12 by dendritic cells. In addition these data suggest that the potency of CD40 mABs[27-29] might be augmented by co-administration of an appropriate bacterial adjuvant in immunotherapy.

For clinical immunotherapeutic application there is a need for a nontoxic and clinical grade stimulus capable of inducing dendritic cells to produce maximum levels of IL 12 when dendritic cells are used as a cellular vaccine. Alternatively, the stimulus should be capable of being applied as a potential systemic adjuvant to a vaccine, which requires the promotion of a Th1 effect. Poly [I]: poly [C] in doses of up to 75 mg/m² intravenously as well as its various stable derivatives (principally dsRNA complexes with polylysine or cellulose) were tested in the 1970s and 1980s in a number of phase 1 and 2 anti-cancer trials. However, these trials had to be abandoned because of the toxic effects of poly[I]: poly[C], which included shock, renal failure and coagulopathies and hypersensitivity reactions[30-32].

Modifications in the structural characteristics of poly[I]: poly [C] by the introduction of unpaired bases (uracil and guanine) has resulted in unique dsRNAs, termed "specifically configured dsRNAs" or "mismatched dsRNAs" [33]. These regions appear to accelerate dsRNA hydrolysis and reduce toxicity in humans [34] whilst retaining ability to promote interferon synthesis. AMPLIGEN® (poly[I]:poly[$C_{12}$U]) is one such synthetic dsRNA containing regularly occurring regions of mismatching (non-hydrogen bonding) along the helical dsRNA chain. AMPLIGEN ® (poly[I]:poly[$C_{12}$U]) exerts immunoregulatory activity, antiviral activity against RNA and DNA viruses and tumour cell antiproliferative activity in vitro and in vivo[33].

Clinical experience with AMPLIGEN® (poly[I]:poly [$C_{12}$U]) currently totals more than 300 patients. No evidence of dose-limiting organ toxicity, including hematological, liver or renal toxicity, has been observed and AMPLIGEN® (poly [I]:poly [$C_{12}$U]) is prepared under GMP conditions for clinical use[34].

The term "specifically configured" as used herein is intended to refer to a double stranded RNA which contains regularly occurring regions of mismatched bases. As there are no hydrogen bonds between the mismatched bases, the double helix is weakened. The half-life of the dsRNA is therefore reduced because it is more easily and quickly degraded, making the dsRNA less toxic to humans and animals.

SUMMARY OF THE INVENTION

According to a first aspect of the invention there is provided a method of producing mature dendritic cells in vitro, the method comprising the step of:
 culturing the immature dendritic cells in the presence of a specifically configured high molecular weight double stranded RNA (dsRNA) polymer.

The specifically configured high molecular weight dsRNA polymer may be selected from the group comprising poly [I]:poly [$C_x$]; poly [I]:poly [$G_x$U]; poly [A]: poly [$U_x$C]; poly [A]:poly [$U_x$G]; poly[U]:poly [ANC]; poly [U]:poly [$I_x$U]; poly [C]:poly [$G_x$A]; poly [C]:poly [$G_x$U]; poly [G]:poly [$C_x$A]; and poly [G]:poly [$C_x$U], where x is on average a number from 3 to 40, and preferably 6 to 20. More preferably, the dsRNA polymer is poly [I]:poly [$C_{12}$U], which is commercially available under the trade name AMPLIGEN® (poly[I]:poly[$C_{12}$U]), or poly [C]:poly [$I_{12}$U]. Typically the dsRNA polymer is poly [I]:poly [$C_{12}$U].

The molecular weight of the dsRNA is typically from 100 to 2 500 kDa, and preferably from 300 to 1 500 kDa.

The immature dendritic cells may be isolated from a human or animal body and may be cultured from peripheral blood mononuclear cells.

The method of producing the mature dendritic cells may activate the mature dendritic cells to produce IL 12 p70 for more than 19 hours, and preferably for more than 43 hours.

According to a second aspect of the invention there is provided a method of producing mature antigen-presenting dendritic cells in vitro, the method including the steps of:
 exposing immature dendritic cells to an antigen; and
 maturing the dendritic cells according to the process substantially as described above.

The antigen may be a cancer antigen, for example a tumour associated antigen. The antigen may alternatively be an antigen derived from a human parasite, virus or microorganism.

The immature dendritic cells may be exposed to the antigen for sufficent time to induce the dendritic cells to capture and process the antigen.

According to a third aspect of the invention, there is provided a method of manufacturing a vaccine for inducing a cellular immune response in a human or animal body, the method including the steps of:
 exposing immature dendritic cells to an antigen in vito until a sufficient number of the dendritic cells become antigen-presenting cells;
 maturing the immature dendritic cells according to the process described above; and including the antigen-presenting mature dendritic cells in a pharmaceutically acceptable formulation.

The antigen may be a cancer-associated antigen, or may be derived from a human or animal parasite, virus or microorganism.

According to a further aspect of the invention there is provided a vaccine including antigen-presenting mature dendritic cells produced by the method substantially as described above.

The vaccine may be for use in a method of treating a patient with cancer or diagnosed with a virus, parasite or microorganism.

The vaccine may further include a suitable diluent, excipient or auxiliary.

The vaccine may also include a suitable bacterial or systemic adjuvant.

According to yet a further aspect of the invention there is provided a method of treating cancer in a human or animal body, the method including the steps of:
culturing immature dendritic cells with a cancer-associated antigen substantially as described above so as to produce tumour antigen-presenting dendritic cells;
maturing the dendritic cells according to a process substantially as described above; and
injecting the human or animal body with the antigen-presenting cells.

According to yet a further aspect of the invention there is provided a method of treating a parasite, virus or microorganism in a human or animal body, the method including the steps of:
culturing immature denditic cells with a parasite-, virus- or microorganism-associated antigen substantially as described above so as to produce antigen-presenting dendritic cells;
maturing the dendritic cells according to a process substantially as described above; and
injecting the human or animal body with the antigen-presenting cells.

DESCRIPTION OF THE INVENTION

The invention will now be described in more detail with reference to FIGS. 1 and 2.

In the figures:
FIG. 1 shows the UV wavelength spectrum for poly [C]: poly [$I_{12}U$];
FIG. 2 shows the UV wavelength spectrum for poly [I]: poly [$C_6U$];
FIG. 3 shows the UV wavelength spectrum for poly [I]: poly [$C_{24}U$];
FIG. 4 shows the effect of poly [I]:poly [C] and AMPLIGEN® (poly[I]:poly[$C_{12}U$]) on immature monocyte-derived dendritic cells as determined by class II and CD83;
FIG. 5 shows the effects on CD83 and class II expression of dendritic cells from healthy individuals treated with poly [I]: poly [$C_6U$], poly [I]: poly [$C_{24}U$] and poly [C]: poly [$I_{12}U$]; and
FIG. 6 shows the influence of maturation agents poly[I]:poly[C] and AMPLIGEN® (poly[I]:poly[$C_{12}U$]) on dendritic cells and the time course of IL 12 p70 production by dendritic cells.

METHODS & MATERIALS

Source of Dendritic Cells:
Peripheral blood mononuclear cells were obtained using leukophoresis. The dendritic cells were cultured from adherent peripheral blood mononuclear cells (using modified Romani's method) in serum-free medium AIM-V (GIBCO) in the presence of 1000 IU/ml GM-CSF (Novartis) and 1000 IU/ml IL 4 (Pharmingen) for 6 to 7 days. An immature dendritic cell population was harvested and split into two equal aliquots. One aliquot was treated with a maturation agent Cells were left in culture at 37° C. for a further two days.

Immunophenotypic Characterisaton of Dendritic Cell Differentiation:
Flow cytometric analysis of dendritic cell differentiation was performed on FACScan (Becton Dickinson) using fluorescein conjugated monoclonal antibodies to CD14, CD1a, CD80, CD86, CD40, CD54, CD83, class I & class II.

Endpoints of Dendritic Cells Maturation:
a) IL 12 production was assayed using an IL 12 p70 ELISA kit assay (R&D Systems). The assay employs the quantitative sandwich enzyme immunoassay designed to measure IL 12 in cell culture supematants.
b) CD83 & upregulation of class II & CD86 expression was determined using flow cytometry.

Source of Maturation Agents:
a) Poly [I]: poly [C] was obtained from Sigma Ltd (UK);
b) AMPLIGEN® (poly [I]: poly [$C_{12}$]) was obtained from Bioclones (Pty) Limited, South Africa;
c) Other specifically configured high molecular weight dsRNA polymers were prepared as described below.

Procedure for Manufacturing Polymer Configurations:
Single-stranded RNA (ssRNA) molecules were synthesized by enzymatic polymerization of nucleotide di-phosphates using the enzyme polynucleotide phosphorylase (EC 2.7.7.8) isolated from *Microccocus luteus*. In the case of specifically configured single-stranded RNA's, containing more than one nucleotide, the polymers were synthesized using the stated molar ratio's of the respective nucleotide-diphosphates. The exact ratios in the final polymer were then determined The single-stranded RNA molecules which were synthesized (poly [$C_6U$], poly [$C_{24}U$] and poly [$I_{12}U$]) are listed in Table 1.

TABLE 1

SINGLE STRANDED RNA CONFIGURATIONS

| ssRNA configuration | Batch No | Total Phos | Endotoxin |
|---|---|---|---|
| Poly [I] | 990420R | 2.5 | |
| Poly [$C_6U$]*(4.5:1) | 20020610F | 2.8 | 0.044 |
| Poly [$C_{24}U$]*(21.6:1) | 20020610G | 3.1 | 0.044 |
| Poly [C] | 20020527E | 2.8 | 0.991 |
| Poly [$I_{12}U$] | 20020603E | 2.4 | 0.031 |

$$*\text{mass ratio} = \frac{\text{desired ratio} - 1.2324}{1.0536}$$

NDP ratio has been corrected by using the preceding formula.
The formula is based on historical determinations of the incorporation of CDP and UDP into ssRNA polymers by polynucleotide phosphorylase.

The single-stranded RNA's were synthesized using polynucleotide phosphorylase at 0.4 Units/ml in a buffer containing 0.1 M Tris pH 9.0, 0.3 M Urea, 7.5 mM $MgCl_2$ and 0.5 mM EDTA.$Na_2$ and the respective nucleoside di-phosphates (NDP's) in the correct proportions to a final concentration of 23.5 mM. The polymerization was carried out at 22-24° C. for 22 to 40 hours, depending on the polymer. During this time, in-process samples were removed to determine the incorporation of NDP into the polymer by HPLC. Viscosity measurements were also taken at specific times. At the end of the polymerization (normally determined by the degree of incorporation of nucleotide di-phosphate), the polymer-containing solution was concentrated 3 fold using a Millipore Minitan apparatus containing a 100 000 nominal molecular weight cutoff membrane. Tris, SDS and phenol were then added to the solution and agitated for 3×60 second intervals. The solution was then centrifuged at 5 000 rpm in a Beckman JA10 rotor and the lower phenol layer removed. Phenol, Tris and SDS were then added and the procedure was repeated 3 times. Following the phenol extraction, the polymer was then precipitated with chilled ethanol after adding KCl to a 0.5 M concentration. The polymer precipitate was re-dissolved and precipitated a second time. The second polymer precipitate was dissolved in water and diafiltered, first against an EDTA buffer to remove any heavy metals, and then against potassium acetate, and finally against 10 volumes of water, before being filtered through a 0.22 μm filter and lyophilized.

Analysis of ssRNA

Each batch of ssRNA was analysed as follows:

Size

The molecules were run on agarose gel electrophoresis to provide an estimate of size for the purposes of matching them with the complimentary strand. All samples were compared to a standard poly $C_{12}U$ material (Batch Number RU040105) with a mean sedimentation coefficient of 6.8 S and a number averaged molecular weight of 500 000 as determined by multi-angle light scattering. Based on the mobility of the samples on agarose gel electrophoresis, the largest and smallest ssRNA's were selected for analytical ultracentrifugation on a Beckman XLA analytical ultracentrifuge. The largest polymer, ooly C, had a mean sedimentation coefficient of 8.9 S and the smallest, poly $I_{12}U$, had a mean sedimentation coefficient of 5.3 S. The remaining polymers are all expected to be within this size range.

Molar Equivalents

Molar equivalents were determined by measuring total phosphorous. This value was used to determine the mass of polymer required in order to achieve an 8 mM polymer concentration during annealing. (i.e. 8 mM with respect to phosphorous [1 phosphorous=1 monomer]). Inorganic phosphorous was also determined in order to ensure accurate determination of organic phosphorous.

Spectral Characteristics

A UV wavelength plot was recorded as a means of identification and also as an assessment of hypochromicity upon annealing of the double stranded polymer.

Base Ratios

The polymers were enzymatically digested to the incorporated nucleotides and run on HPLC to demonstrate base purity and also base ratios of those polymers with a deliberate incorporation of more than one base in the single-strand Endotoxin The endotoxin was determined using the Cape Cod LAL methods (as endotoxin itself can induce maturation of dendritic cells, it was important that the polymers were essentially endotoxin free).

Annealing of dsRNA

Annealing was performed in AMPLIGEN® (poly[I]:poly[$C_{12}$U]) buffer containing 10 mM sodium phosphate (pH 7.4), 150 mM sodium chloride and 1 mM magnesium chloride. Polymers were dissolved to 8 mM with regard to total organic phosphorous at 50° C. and annealed by mixing equal volumes of the respective complimentary ssRNA solutions, heating to 65° C. for 10 minutes and then cooling to room temperature. The material was then filtered through a 0.22 pm filter and vialed under laminar flow.

Analysis of dsRNA

Spectral

Figure 2:
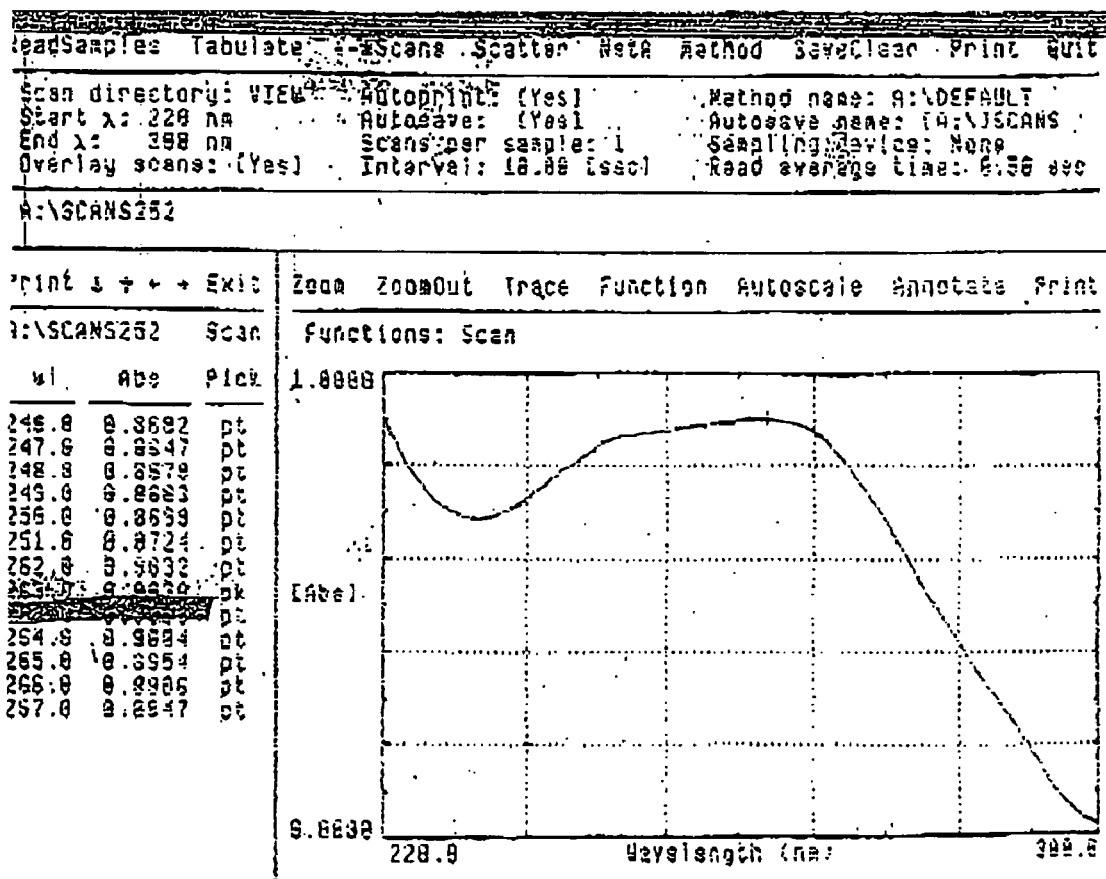
Figure 3:
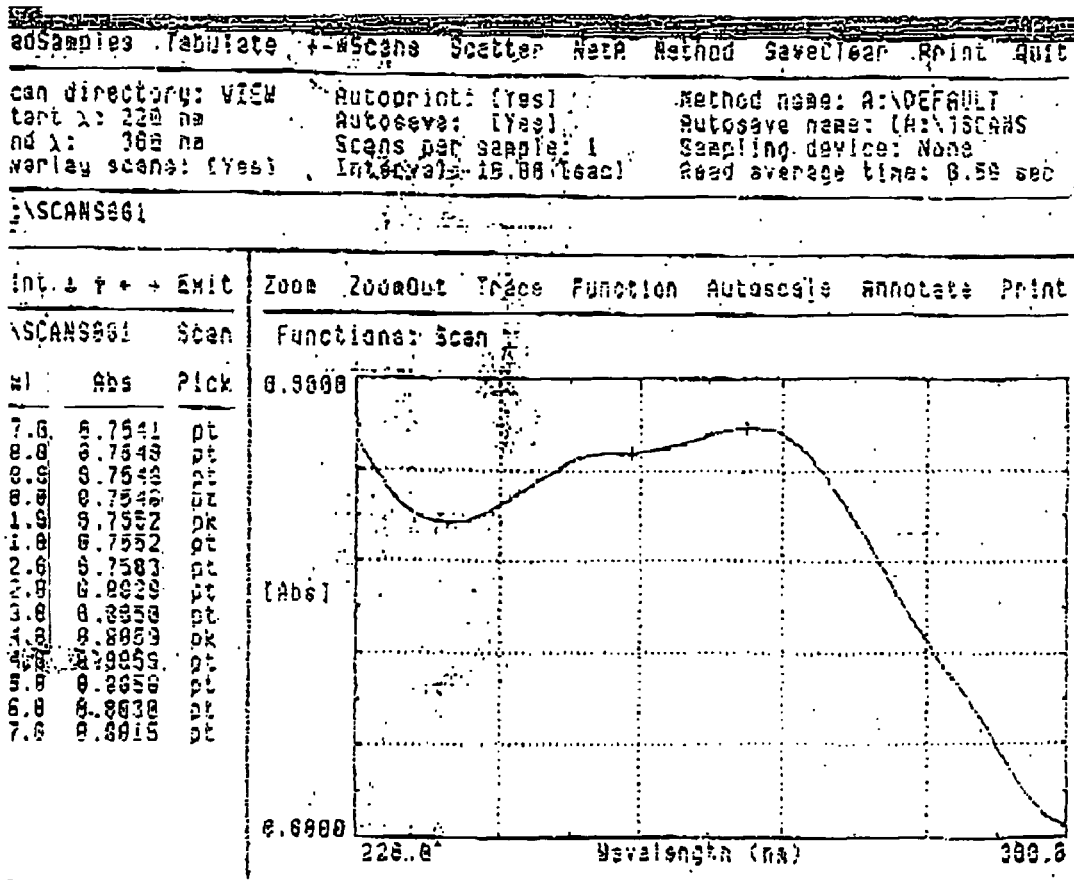

Samples of the two ssRNA solutions prepared for annealing as well as the annealed dsRNA were taken and the UV wavelength profile assessed (FIGS. 1 to 3). The hypochromic shift (generally at the peak absorbance of the ssRNA) was evaluated as an indication of annealing.

Endotoxin

Endotoxin of the dsRNA was assessed using the Cape Cod LAL assay.

Concentration

Concentration was assumed to be equivalent to the starting concentration of the ssRNA entities.

TABLE 2

Analysis of dsRNA

| dsRNA configuration | Batch No. | Endotoxin (EU/ml) | Concentration | Hypo-chromicity |
|---|---|---|---|---|
| Poly [C]: Poly [$I_{12}$U] | 20020626C | 4 | 8 mM (2.5 mg/ml) | 0.77 |
| Poly [I]: Poly [$C_6$U] | 20020626D | 1 | 8 mM (2.5 mg/ml) | 0.88 |
| Poly [I]: Poly [$C_{24}$U] | 20020626E | 1 | 8 mM (2.5 mg/ml) | 0.79 |

The reduced hypochromic shift obtained for poly [I]: poly [$C_6$U] can be explained by the increased frequency of the uridine mismatch in the double stranded RNA, which will yield a higher proportion of single stranded RNA in the dsRNA chain when compared to a more fully base-paired polymer such as poly [I]: poly [$C_{12}$U] or poly [I]: poly [$C_{24}$U].

Experimental Studies (a) Comparison of dendritic cell maturation effects of AMPLIGEN® (poly[I]:poly[$C_{12}$U]) and other high molecular weight specifically configured dsRNA polymers and poly [I]: poly [C] on immature monocyte-derived dendritic cells:

A direct comparison of poly [I]: poly [$C_{12}$U], poly [C]: poly [$I_{12}$U], poly [I]: poly [$C_6$U], poly [I]: poly [$C_{24}$U] and poly [I]: poly [C] as the maturation agents for human monocyte derived dendritic cells, as determined by changes in cell surface phenotype, was conducted using FACS analysis.

Immature dendritic cells were generated by culturing leucophoresed peripheral blood mononuclear cells in the presence of GM-CSF and IL 4 for seven days. The maturation stimulus was introduced in culture for 48 hours in a uniform culture condition, utilizing poly [I]: poly [C] in one test and poly [I]: poly [$C_{12}$U], poly [C]: poly [$I_{12}$U], poly [I]: poly [$C_8$U] and poly [I]: poly [$C_{24}$U] in other tests. Using FACS analysis, the phenotype of the mature dendritic cells was determined (FIGS. 4 and 5). The mature dendritic cells were identified as strongly positive for CD83 (a glycoprotein expressed predominately on the surface of mature dendritic cells). Class II molecules were also up-regulated compared with immature dendritic cells (untreated). No evidence of cellular toxicity was seen at the dose levels tested.

(b) Comparison of time course of poly[I]:poly[C] and AMPLIGEN® (polyl[I]:poly[$C_{12}$U]) (and other high molecular weight specifically configured dsRNA polymers) on dendritic cell maturation and IL 12 production:

Mononuclear cells were isolated by density gradient centrifugation. Adherent cells were cultured for six days in the presence of IL 4 and GM-CSF. Cells were harvested after immunophenotypic characterisation (immature) and recultured in serum-free medium in the presence of IL 4 and GM-CSF. Three separate plates of the cells were prepared as follows:

plate one—no treatment;
plate two—poly [I]: poly [C] (100 μg/ml);
plate three—poly [I]: poly [$C_{12}$U] (250 μg/ml).

Seven hours after the addition of the maturation agent, the culture medium was removed from each plate and fresh medium without the maturation agent was added. This was repeated at time intervals and the IL 12 production was determined on each culture supernatant collected.

Results

Maturation Effect:

The FACS analysis results comparing poly [I]: poly [$C_{12}$U], poly [C]: poly [$I_{12}$U], poly [I]: poly [$C_6$U], poly [I]: poly [$C_{24}$U] and poly [I]: poly [C] as maturation agents for human monocyte-derived dendritic cells are summarized and illustrated in FIGS. 4 and 5.

Compared to the untreated dendritic cells, poly [I]:poly [C], AMPLIGEN® (poly [I]: poly[$C_{12}$U]), poly [C]: poly [$I_{12}$U], poly [I]: poly [$C_6$U] and poly [I]: poly [$C_{24}$U] produced a significantly greater level of expression of the two markers, with a higher amplitude response being associated with AMPLIGEN® (poly[I]:poly [$C_{12}$U]), poly [C]: poly [$I_{12}$U], poly [I]: poly [$C_6$U] and poly [I]: poly [$C_{24}$U].

IL 12 (D70) Production:

Over the time course studied, the untreated dendritic cells did not produce any IL 12 as detectable by the specific ELISA technique. The poly [I]:poly [C] and AMPLIGEN® (poly[I]: poly[$C_{12}$U]) did not show any IL 12 production at 4 hours. However, they both produced significant and equally high levels of IL 12 at 19 hours. The IL 12 level was subsequently lower at 27 hours and continued to drop at 43 hours. The overall fall in production level at each time point was more marked with poly [I]:poly [C] compared with AMPLIGEN® (poly[I]:poly[$C_{12}$U])

The results show for the first time the capacity of AMPLIGEN® (poly[I]:poly[$C_{12}$U]) to cause both phenotypic maturation of dendritic cells and activation of IL 12 production in these cells. AMPLIGEN® (poly[I]:poly[$C_{12}$U]) is also shown to have a greater capacity to mature dendritic cells compared to poly [I]:poly [C]. Furthermore, the IL 12 production induced by AMPLIGEN® (poly[I]:poly[$C_{12}$U]) appears to be sustained for a longer period compared with that associated with poly [I]:poly [C].

The overall findings indicate that AMPLIGEN® (poly[I]: poly[$C_{12}$U]), with its non toxic clinical profile, possesses significant potential as an agent for causing dendritic cell maturation and activation of IL 12 production, two attributes which are believed to be important in optimal priming and induction of antigen-specific cytotoxic T-cell response by antigen-primed dendritic cells. Furthermore, as AMPLIGEN® (poly[I]:poly[$C_{12}$U]) is manufactured to a clinical grade and has a non toxic clinical profile, it is suitable for use together with dendritic cells which are intended for use in a vaccine.

A vaccine for stimulating the cellular immune response in patient's diagnosed with cancer can be produced. In the method of producing the vaccine, immature dendritic cells are exposed to the patient's tumour-associated antigens to produce tumour antigen presenting immature dendritic cells. The antigen presenting dendritic cells are then matured in the presence of AMPLIGEN® (poly[I]:poly[$C_{12}$U]) by the method described above, and then included in a pharmaceutical formulation in the form of a vaccine. The vaccine can then be injected into the patient, whereupon it is expected that the mature dendritic cells will migrate to the patient's regional lymph nodes to induce CTL response.

The applicant believes that poly [I]: poly [$C_{12}$U], poly [C]: poly [$I_{12}$U), poly [I]: poly [$C_6$U] and poly [I]: poly [$C_{24}$U] are representative of the class of specifically configured high molecular weight dsRNA polymers, and from the results shown it is to be expected that other specifically configured high molecular weight dsRNA polymers will also be suitable for maturing dendritic cells. Examples of such specifically configured high molecular weight dsRNA polymers are poly [I]: poly [$C_x$U]; poly [I]: poly [$G_x$U]; poly [A]: poly [$U_x$C]; poly [A]: poly [$U_x$G]; poly [U]: poly [$A_x$C]; poly [U]: poly [$I_x$U]; poly [C]: poly [$G_x$A]; poly [C]poly [$G_x$U]; poly [G]: poly [$C_x$A]; and poly [G]: poly [$C_x$U], where x is on average a number from 3 to 40, preferably 6 to 20, and the dsRNAs have on average a molecular weight of from 100 to 2,500 kDa, and preferably 300 to 1 500 kDa.

REFERENCES

1. Zinkemagel R M, Doherty P C. MHC—restricted cytotoxic T cell studies on the biological role of polymorphic major transplantation antigens determining T-cell restriction specificity, function and responsiveness. Adv Immunol 1979:27: 51-177.
2. Banchereau J, Steinman R M. DC and the control of immunity. Nature 1998: 392: 245-252.
3. Carbone F R, Kurts C, Bennett S R et al. Cross presentation: a general mechanism for CTL immunity and tolerance. Immunol Today 1998; 19 (8): 368-373.
4. Mayodormo I, Zorina, T, Storkus W J, Zitvogel, L, Celluzzi C, Falo L D, Melief C, Ildstad S T, Kast W M, Deleo A B. Bone marrow-derived dendritic cells pulsed with synthetic tumour peptides elicit protective and therapeutic anti-tumour immunity. Nature Medicine 1995; 1 (12): 1297-1302.
5. Zitvogel L, Mayordomo J I, Tjandrawan T et al. Therapy of murine tumors with tumor derived peptide pulsed dendritic cells: dependence on T cells. B7 costimulation and Th 1 associated cytokines. J exp Med 1996; 183:87-97.
6. Nestle F O, Alijagic S, Gilliet M et al. Vaccination of melanoma patients with peptide-or tumor lysate pulsed DC, Nat Med 1998; 4:328
7. Thurner B. Haendle I, Roder C D et al. Vaccination with Mage-3A1 peptide pulsed mature monocyte derived DC expands specific cytotoxic T cells and induces regression of some metastases in advanced stage 4 melanoma. J Exp Med 1999; 190: 54-59.
8. Kugler A, Stuhler G, Walden P, et al. Regression of human metastatic renal cell carcinoma after vaccination with tumour cell-dendritic cell hybrids. Nat Med 2000; 6: 332-336.
9. Murphy G P, Tjoa B A, Simmons S J et al. Phase 11 prostate cancer vaccine trial: report of study involving 37 patients with disease recurrence following primary treatment. Prostate 1999; 39;54-59.
10. Adams M de Jong A, Navabi H, Lippetz C, B Jasani, B, Man S, Fiander A, R Bailey Wood, van der Burg S H, A Burnet Evans A S, Mason M. In vivo induction of HPV 16 specific (CTL) and T helper cell responses in patients with advanced cervical cancer using autologous dendritic cells (DC) pulsed with autologous or allogeneic tumour lysate as a potential anti-cancer vaccine. In preparation.
11. Zitvogel L, Angevin E, T Tursz. Dendritic cell-based immunotherapy of cancer. Annals of Oncology 2000; 11 (supplement 3); 199-205.

12. Steinman R. M. Dendritic cells In Fundamental Immunology (Paul, W. E., Ed) 1999; Lippinscott-Raven pp. 547-573.
13. Dhodapkar M V, Steinman R M, Sapp M, Desai H, Fossella C, Krasovsky J, Donahoe S M, Dunbar P R, Cerundolo V, Nixon D F. Rapid generation of broad T cell immunity in humans after a single injection of mature dendritic cells J Clin Invest 1999; 104; 173-80.
14. Steinbrink K, Jonuleit H, Moller, Schuler G, Knop J, Enk A H. Interleukin 10 treated human dendritic cells induce a melanoma-antigen specific anergy in CD8+ T cells resulting in failure to lyse tumour cells. Blood 1999; 93(5): 1634-42.
15. Matzinger P. Tolerance, danger, and the extended family. Annu. Rev. Immunol. 1994; 12: 991-1045.
16. Sparwasser T. Koch E S, Vabulas R M, Heeg K, G B, Lipford G B, Ellwart J W, H Wagner. Bacterial DNA and immunostimulatory CpG oligonucleotides trigger maturation and activation of murine dendritic cells Eur J Immunol 1998; 28:2045.
17. Ridge J P, Dirosa F, Matzinger P. A conditioned dendritic cell can be a temporal bridge between a CD4 (+) T helper and a T-Killer cell. Nature 1998; 393: 474.
18. Cella M, An Engering A, V PinetV, Pieters J, Lanzavecchia A. Inflamatory stimuli induce accumulation of MHC class II complexes on dendritic cells. Nature 1997; 388: 782.
19. Basu S et al. Necrotic but not apoptotic cell death releases heat shock proteins which deliver partial maturation signal to dendritic cells and activates the NF-kappa B pathway. Int lmmunol.2000; 12, 1539-1408.
20. Sallusto F. Lanzavecchia A. Efficient presentation of soluble antigen by cultured human dendritic cells is maintained by granulocyte/macrphage colony stimulating factor plus interleukin 4 and down regulated by tumor necrosis factor. J Exp Med 1994; 179 :1109
21. Luft T, Pang K C, Thomas E, Hertzog P, Hart D N J, Trapani, J Cebon J. Type 1 IFNs enhance the terminal differentiation of dendritic cells .J Immunol 1998; 161: 1947.
22. Romani N, D Reider D, Heuer M, Ebner S, E Kämpgen E, Eibl B, Neiderwieser D. Schuler G. Generation of mature dendritic cells from human blood: An improved method with special regard to clinical applicability J Immunol Methods 1996; 196: 137
23. Verijk R W, Mutis M , Esendam B, Kamp J, Melief J M, Cees, Brand A, Goulmy E. Polyribosinosinic Polyribocytidlic (Poly I:C) induces stable maturation of functionally active human dendritic cells. Journal of Immunology 1999; 163:57-61.
24. Schulz O, Edwards A D, Schito M, Aliberti J, Manickasingham S. Sher A, Reis e Souza C (2000) CD40 triggering of heterodimeric IL-12 p70 production by dendritic cells in vivo requires a microbial priming signal. Immunity 2000; 13:453-462.
25. Hilkens C M, Kalinski P. de Boer M, Kapsenberg M. Human dendritic cells require exogenous interleukin-12—inducing factors to direct the development of naïve T-helper cells toward the Th1 phenotype. Blood 1997; 90:1920-1926.
26. Sniggers A, Kalinski P; C M Hilkens C M, Kapsenberg M L High level IL12 production by human dendritic cells requires two signals. Int. Immunol 1998: 10: 1593-1598.
27. Diehl L, den Boer A T, Schoenberger S P, van der Voort E I, T N Schumacher T N, Melief C J, Offringa R, Toes R E. CD40 activation in vivo overcomes peptide-induced peripheral cytotoxic T-lymphocyte tolerance and augments anti-tumour vaccine efficacy. Nat. Med 1999; 5; 774-779.
28. French R R, Chan H T, Tutu A L, Gleennie M J. CD40 antibody evokes a cytotoxic T-cell response that eradicates lymphoma and bypasses T cell help. Nat Med 1999; 5: 548-553.
29. Sotomayor E M, Borello I, E Tubb E, F M Rattis F M, Bien H, Lu Z, S Fain S, Schoenberger S, Levitsky H I. Conversion of tumor specific CD4+ tolerance to T-cell priming. Through in vivo ligation of CD40. Nat Med 1999; 5: 780-787.
30. Robinson R A, De Vita V T, H Levy H B, Baron S, Hubbard S P, Levine A S. Brief communication A Phase 1-11 Trial of multiple-Dose Polyribosinosinic-Polyribocytidylic acid in patients with leukaemia or solid tumors .J Natl Cancer Inst 1976; 57:599-602.
31. Krown S E, Friden G B Khansur T et al. T at al. Phase 1 trial with interferon inducer PolyI: C/poly-L-lysine (poly ICL). J IFN Res 1983; 3:281-90
32. Levy H B, Riley F L, Utilisation of stabilised forms of polynucleotides. In: Cane P E, Carter W A Eds. Handbook of experimental pharmacology, 1984 Berlin; Springer Verlag pp. 515-33.
33. Strayer D R, Carter W A, Brodsky I, Dheyney P, Petersen D, Salvato P, Thompson C, Loveless M, Shapiro D E. Elsasser W, Gillespie DH.A. Controlled clinical trial with specifically configured RNA drug Poly (I): Poly ($C_{12}$U), in Chronic Fatigue Syndrome Clinical Infectious Diseases 1994: 18 (Suppl 1): S 88-95.
34. Ampligen® poly [I]: poly [C12 U] Clinical Investigators Brochure Bioclones (Pty) Ltd 1998.

The invention claimed is:

1. A method for promoting the maturation of immature dendritic cells in vitro, the method comprising:
    exposing immature dendritic cells to an antigen;
    culturing the immature dendritic cells in the presence of a specifically configured high molecular weight double stranded RNA (dsRNA) polymer having a molecular weight from 300kDa to 2500kDa, in order to induce the maturation of immature dendritic cells into mature dendritic cells that produce IL-12 (p70),
    wherein IL-12 (p70) production by mature dendritic cells exposed to the specifically configured high molecular weight (dsRNA) polymer is sustained at a higher level over a 43 hour period than dendritic cells matured by exposure to poly[I]: poly[C].
2. The method according to claim 1, wherein the specifically configured high molecular weight dsRNA polymer is selected from the group consisting of
    poly [I]:poly [CxU];
    poly [I]:poly [GxU];
    poly [A]:poly [UxC];
    poly [A]:poly [UxG];
    poly [U]:poly [AxC];
    poly [U]:poly [IxU];
    poly [C]:poly [GxA];
    poly [C]:poly [GxU];
    poly [G]:poly [CxA]; and
    poly [G]:poly [CxU], where x is on average a number from 3 to 40.
3. The method according to claim 2, wherein x is a number from 6 to 20.
4. The method according to claim 1, wherein the dsRNA polymer is selected from the group consisting of poly [I]:poly [C12U] and poly [C]:poly [I12U].
5. The method according to claim 1, wherein the molecular weight of the dsRNA is from 300 to 1500 kDa.

6. The method according to claim 1, wherein the immature dendritic cells are cultured from peripheral blood mononuclear cells isolated from a human or an animal.

7. The method according to claim 1, wherein the antigen is a cancer antigen.

8. The method according to claim 1, wherein the antigen, which is derived from a human or an animal, is selected from the group consisting of human parasite antigens, animal parasite antigens, human virus antigens, animal virus antigens, human microorganism antigens, and animal microorganism antigens.

9. The method according to claim 1, wherein the exposing the immature dendritic cells to the antigen is for a sufficient time to induce the dendritic cells to capture and process the antigen.

10. A method of manufacturing a vaccine in a human or an animal, the method comprising:
    exposing immature dendritic cells to an antigen in vitro to produce a sufficient number of antigen-presenting immature dendritic cells;
    promoting the maturation of immature dendritic cells according to the method of claim 1 to produce antigen-presenting mature dendritic cells; and
    including the antigen-presenting mature dendritic cells in a pharmaceutically acceptable formulation.

11. The method according to claim 10, wherein the antigen, which is derived from a human or an animal, is selected from the group consisting of cancer-associated antigens, human parasite antigens, animal parasite antigens, human virus antigens, animal virus antigens, human microorganism antigens, and animal microorganism antigens.

12. A vaccine manufactured by the method of claim 10.

13. The vaccine according to claim 12, further comprising:
    a diluent, an excipient, an auxiliary adjuvant, a bacterial adjuvant, and/or a systemic adjuvant.

14. A method of treating a human or an animal afflicted with cancer, the method comprising:
    culturing immature dendritic cells with a cancer-associated antigen to produce tumour antigen-presenting dendritic cells;
    promoting the maturation of dendritic cells according to the method of claim 1; and
    injecting the human or animal with the antigen-presenting dendritic cells.

15. A method of treating a human or an animal infected with a parasite, a virus, or a microorganism, the method comprising:
    culturing immature dendritic cells with an antigen derived from a parasite, a virus, or a microorganism to produce antigen-presenting dendritic cells;
    promoting the maturation of dendritic cells according to the method of claim 1; and
    injecting the human or animal with the antigen-presenting dendritic cells.

* * * * *